US007495100B2

(12) United States Patent
Cushman et al.

(10) Patent No.: US 7,495,100 B2
(45) Date of Patent: Feb. 24, 2009

(54) SYNTHESIS OF INDENOISOQUINOLINES

(75) Inventors: Mark S. Cushman, West Lafayette, IN (US); Andrew E. Morrell, Bristol, TN (US); Yves G. Pommier, Bethesda, MD (US)

(73) Assignees: Purdue Research Foundation, West Lafayette, IN (US); The United States of America as represented by the Department of Health and Human Services, Washington, DC (US)

( * ) Notice: Subject to any disclaimer, the term of this patent is extended or adjusted under 35 U.S.C. 154(b) by 305 days.

(21) Appl. No.: 11/125,723

(22) Filed: May 9, 2005

(65) Prior Publication Data

US 2006/0025595 A1 Feb. 2, 2006

Related U.S. Application Data

(60) Provisional application No. 60/568,987, filed on May 7, 2004, provisional application No. 60/572,852, filed on May 20, 2004.

(51) Int. Cl.
*C07D 221/08* (2006.01)
(52) U.S. Cl. .................................... 546/61
(58) Field of Classification Search .............. 546/61
See application file for complete search history.

(56) References Cited

U.S. PATENT DOCUMENTS

| 5,597,831 A | 1/1997 | Michalsky et al. |
| 6,509,344 B1 | 1/2003 | Cushman et al. |

FOREIGN PATENT DOCUMENTS

| WO | WO 00/21537 | 4/2000 |
| WO | WO 01/30753 | 5/2001 |
| WO | WO 03/051289 | 6/2003 |
| WO | WO 2004/014862 | 2/2004 |
| WO | WO 2004/014906 | 2/2004 |
| WO | WO 2004/014918 | 2/2004 |

OTHER PUBLICATIONS

Cushman et al., "Stereoselective Oxidation by Thionyl Chloride Leading to the Indeno[1,2-c]isoquinoline System," *J. Org. Chem.*, 1978, vol. 43, No. 19, pp. 3781-3783.
Cushman et al., "Total Synthesis of Nitidine Chloride," *J. Org. Chem.*, 1978, vol. 43, No. 2, pp. 286-288.
Cushman et al., "Synthesis of New Indeno[1,2-c]isoquinolines: Cytotoxic Non-Camptothecin Topoisomerase I Inhibitors," *J. Med. Chem.*, 2000, vol. 43, No. 20, pp. 3688-3698.
Kohlhagen et al., "Protein-Linked DNA Strand Breaks Induced by NSC 314622, a Novel Noncamptothecin Topoisomerase I Poison," *Mol. Pharmacol.*, 1998, vol. 54, pp. 50-58.
Staker et al., "The Mechanism of Topoisomerase I Poisoning by a Camptothecin Analog," *Proc. Natl. Acad. Sci. U.S.A.*, 2002, vol. 99, No. 24, pp. 15387-15392.

Nagarajan et al., "Design, Synthesis, and Biological Evaluation of Indenoisoquinoline Topoisomerase I Inhibitors Featuring Polyamine Side Chains on the Lactam Nitrogen," *J. Med. Chem.*, 2003, vol. 46, No. 26, pp. 5712-5724.
Shetty et al., "Aromatic π-Stacking in Solution as Revealed through the Aggregation of Phenylacetylene Macrocycles," *J. Am. Chem. Soc.*, 1996, vol. 118, No. 5, pp. 1019-1027.
Vance et al., "Structural Features of Nitroaromatics That Determine Mutagenic Activity in *Salmonella typhimurium*," *Environmental Mutagenesis*, 1984, vol. 6, pp. 797-811.
Whitmore et al., "The Preparation of Homophthalyl Cyclic Hydrazide and 4-Aminohomophthalyl Cyclic Hydrazide," *J. Am. Chem. Soc.*, 1944, vol. 66, pp. 1237-1240.
Strumberg et al., "Synthesis of Cytotoxic Indenoisoquinoline Topoisomerase I Poisons," *J. Med. Chem.*, 1999, vol. 42, No. 3, pp. 446-457.
Nagarajan et al., "Synthesis and Anticancer Activity of Simplified Indenoisoquinoline Topoisomerase I Inhibitors Lacking Substituents on the Aromatic Rings," *J. Med. Chem.*, 2004, vol. 47, No. 23, pp. 5651-5661.
Jayaraman et al., "Synthesis of New Dihydroindeno [1,2-c]isoquinoline and Indenoisoquinolinium Chloride Topoisomerase I Inhibitors Having High In Vivo Anticancer Activity in the Hollow Fiber Animal Model," *J. Med. Chem.*, 2002, vol. 45, No. 1, pp. 242-249.
Fox et al., "Design, Synthesis, and Biological Evaluation of Cytotoxic 11-Alkenylindenoisoquinoline Topoisomerase I Inhibitors and Indenoisoquinoline-Camptothecin Hybrids," *J. Med. Chem.*, 2003, vol. 46, No. 15, pp. 3275-3282.
Kubova et al., "Binding Properties of Nitidine and Its Indenoisoquinoline Analogue with DNA," *Studia Biophs.*, 1986, vol. 114, No. 1-3, pp. 251-256.
Anthony et al., "Differential Induction of Topoisomerase I-DNA Cleavage Complexes by the Indenoisoquinoline MJ-III-65 (NSC 706744) and Camptothecin: Base Sequence Analysis and Activity Against Camptothecin-Resistant Topoisomerase I," *Cancer Res.*, 2003, vol. 63, pp. 7428-7435.
Cho et al., "A Novel Synthesis of Benzo[c]phenanthridine Skeleton and Biological Evaluation of Isoquinoline Derivatives," *Chem. Pharm. Bull.* vol. 47, No. 6, pp. 900-902 (1999).
Shamma et al., "Synthetic Approaches to Camptothecin," *Tetrahedron*, vol. 25, pp. 2275-2279 (1969).
Dyke et al., "The Chemistry of Cryptopine-I: The Epicryptopines," *Tetrahedron*, vol. 24, pp. 1455-1465 (1968).
Cushman et al., "Synthesis and Antitumor Activity of Structural Analogues of the Anticancer Benzophenanthridine Alkaloid Fagaronine Chloride," *J. Med. Chem.*, 1985, vol. 28, No. 8, pp. 1031-1036.

(Continued)

*Primary Examiner*—Zinna N Davis
(74) *Attorney, Agent, or Firm*—Barnes & Thornburg LLP

(57) ABSTRACT

Indenoisoquinolines and dihydroindenoisoquinolines are described. In particular, such compounds possessing one or more electron withdrawing substituents are described. The in vitro anticancer activities of these molecules tested in the National Cancer Institute's screen of 55 cell lines is described. The compounds tested for topoisomerase I (top1) inhibition is described.

10 Claims, No Drawings

OTHER PUBLICATIONS

Wawzonek et al., "The Synthesis and Reactions of 1-Carbamyl-11-ketoindeno[1,2-c]isoquinoline," *J. Org. Chem.*, 1966, vol. 31, pp. 1004-1006.

Patel et al., "Neuromuscular blocking activity of *bis*-4-benzyltetrahydroisoquinolinium esters in the cat," *European Journal of Pharmaceutical Sciences*, vol. 4 (1996), 63-71.

Corey et al., "A Total Synthesis of Natural 20(*S*)-Camptothecin," *J. Org. Chem.*, vol. 40, No. 14, 1975, pp. 2140-2141.

Xiao et al., "Dihydroindenoisoquinolines function as prodrugs of indenoisoquinolines," *Bioorganic & Medicinal Chemistry Letters*, vol. 15 (2005), 2795-2798.

Staker et al., "Structures of Three Classes of Anticancer Agents Bound to the Human Topoisomerase I-DNA Covalent Complex," *J. Med. Chem.*, 2005, vol. 48, No. 7, 2336-2345.

Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex As Determined by X-ray Crystallographic Analysis," *J. Med. Chem.*, 2005, vol. 48, No. 15, 4803-4814.

Xiao et al., "On the Binding of Indeno[1,2-c]isoquinolines in the DNA-Topoisomerase I Cleavage Complex," *J. Med. Chem.*, 2005, vol. 48, No. 9, 3231-3238.

Antony et al., "Cellular Topoisomerase I Inhibition and Antiproliferative Activity by MJ-III-65 (NSC 706744), an Indenoisoquinoline Topoisomerase I Poison," *Molecular Pharmacology*, 2005, vol. 67, No. 2, 523-530.

Hertzberg et al., "On the Mechanism of Topoisomerase I Inhibition by Camptothecin: Evidence for Binding to an Enzyme-DNA Complex," *Biochemistry*, 1989, vol. 28, No. 11, 4629-4638.

Wang et al., "Differential Effects of Camptothecin Derivatives on Topoisomerase I-Mediated DNA Structure Modification," *Biochemistry*, 1998, vol. 37, No. 26, 9399-9408.

Wang et al., "Role of the 20-Hydroxyl Group in Camptothecin Binding by the Topoisomerase I-DNA Binary Complex," *Biochemistry*, 1999, vol. 38, No. 14, 4374-4381.

Morrell et al., "Synthesis of nitrated indenoisoquinoles as topoisomerase I inhibitors," *Bioorganic & Medicinal Chemistry Letters*, vol. 14 (2004), 3659-3663.

Xiao et al., "Design, synthesis, and biological evaluation of cytotoxic 11-aminoalkenylindenoisoquinoline and 11-diaminoalkenylindenoisoquinoline topoisomerase I inhibitors," *Bioorganic & Medicinal Chemistry*, vol. 12 (2004), 5147-5160.

Pourquier et al., "Induction of Reversible Complexes between Eukaryotic DNA Topoisomerase I and DNA-containing Oxidative Base Damages," *The Journal of Biological Chemistry*, vol. 274, No. 13, 1999, pp. 8516-8523.

Cushman et al., "Synthesis and Biological Activity of Structural Analogues of the Anticancer Benzophenanthridine Alkaloid Nitidine Chloride," *J. Med. Chem.*, 1984, vol. 27, No. 4, 544-547.

Hertzeg et al., "Modification of the Hydroxy Lactone Ring of Camptothecin: Inhibition of Mammalian Topoisomerase I and biological Activity," *J. Med. Chem.*, 1989, vol. 32, No. 3, 715-720.

Somekawa et al., "Intramolecular [2+2]Photocycloadditions of 1-(ω-Alkenyl)-2-pyridones Possessing an Ester Group on the Olefinic Carbon Chain," *J. Org. Chem.*, 1992, vol. 57, No. 21, 5708-5712.

Canan Koch et al, "Enantioselective Preparation of β-Alkyl-γ-butyrolactones from Functionalized Ketene. Dithioacetals," *J. Org. Chem.*, 1993, vol. 58, No. 10, 2725-2737.

Jayaraman et al., "Novel Oxidative Transformation of Indenoisoquinolines to Isoquinoline-3-spiro-3'-phthalides in the Presence of Osmium Tetraoxide and 4-methylmorpholine *N*-Oxide," *J. Org. Chem.*, 1998, vol. 63, No. 17, 5736-5737.

Xiao et al., "Novel Autoxidative Cleavage Reaction of 9-Fluoredenes Discovered during Synthesis of a Potential DNA-Threading Indenoisoquinoline," *J. Org. Chem.*, 2004, vol. 69, No. 22, 7495-7501.

Li et al., "Synthesis of the Tricyclic ABC Ring Subunit of Mazamine A," *Tetrahedron*, vol. 54 (1998), 6661-6676.

Pommier et al., "Mechanism and action of eukaryotic DNA topoisomerase I and drugs targeted to the enzyme," *Biochem. Biophys. Acta.*, 1400, 83-106 (1998).

Pommier et al, Editorial Overview "Topoisomerase Inhibitors: Why New Ones?", Opinion in Oncologic, Endocrine & Metabolic Investigational Drugs, 1(2), 168-169 (1999).

SYNTHESIS OF INDENOISOQUINOLINES

CROSS REFERENCE TO RELATED APPLICATION

This application claims priority to U.S. Provisional Applications, Ser. Nos. 60/568,987, filed May 7, 2004, and 60/572,852, filed May 20, 2004, the disclosures of which are incorporated herein by reference.

GOVERNMENT RIGHTS

Research relating to this invention was supported in part by the National Institutes of Health (NIH) under Research Grant No. U01 CA89566 and Training Grant No. ST32 CA09634-12, and National Cancer Institute (NCI), Developmental Therapeutics Program, DCTD, under Contract NO1-CO-56000. The U.S. Government may have certain rights in this invention.

TECHNICAL FIELD

The present invention relates to cytotoxic indenoisoquinolines and dihydroindenoisoquinolines, and methods for preparing such compounds.

BACKGROUND

The indenoisoquinolines are a class of cytotoxic molecules that have been demonstrated to inhibit topoisomerase I (top1) by intercalating between DNA bases at the enzyme's cleavage site. This mechanism of action is similar to the natural product camptothecin (1) and its clinically useful derivative topotecan (2) (see Kohlhagen G, et al., *Mol. Pharmacol.* 1998, 54, 50, incorporated herein by reference).

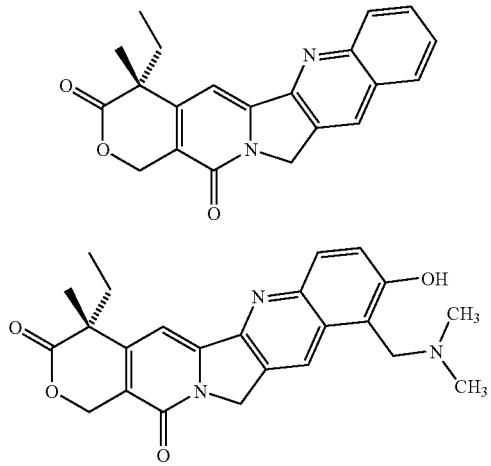

Thus, the indenoisoquinolines constitute a novel class of non-camptothecin top1 inhibitors. Mechanistically, the intercalation of these molecules elongates the DNA such that top1 cannot catalyze the religation of the DNA backbone (Staker B, et al., *Proc. Natl. Acad. Sci. U.S.A.* 2002, 99, 15387). These inhibitors are therefore classified as top1 "poisons" as opposed to top1 "suppressors", the latter of which inhibit the DNA cleavage reaction.

Indenoisoquinolines have been synthesized using methylenedioxy and di(methoxy) substituents as well as molecules that lack substituents on both the isoquinoline and indenone rings. Past synthetic efforts have focused on exploring the substitution pattern of the lactam nitrogen with a wide variety of carbon and heteroatom substituents. These efforts have resulted in the ability to potentiate the cytotoxicity and top1 inhibition of the indenoisoquinolines through the prudent selection of functionalities protruding from the lactam nitrogen.

SUMMARY OF THE INVENTION

Processes for preparing indenoisoquinolines and dihydroindenoisoquinolines are described. In one embodiment, processes for preparing indenoisoquinolines and dihydroindenoisoquinolines that are substituted with at least one electron withdrawing group are described. In another embodiment, processes for preparing indenoisoquinolines and dihydroindenoisoquinolines that are substituted with at least one nitrogen containing group are described.

In one illustrative process for preparing a dihydroindenoisoquinolines, the process comprises the step of cyclizing a compound of the formula

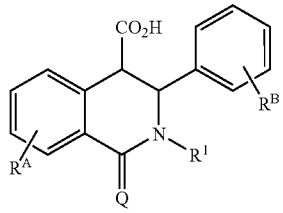

by reacting the compound with phosphorus pentoxide in an aprotic solvent, wherein Q, $R^A$, $R^B$, and $R^1$ are as described herein.

In one illustrative process for preparing a indenoisoquinolines, the process comprises the steps of (a) activating a compound of the formula

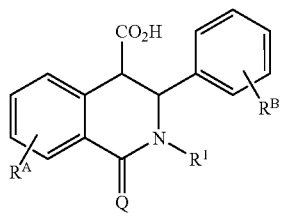

by reacting the compound with a carboxylic acid activating reagent to form an activated carboxylic acid derivative; and (b) cyclizing the activated carboxylic acid derivative by reacting the activated carboxylic acid derivative with a Lewis acid, wherein Q, $R^A$, $R^B$, and $R^1$ are as described herein.

In another embodiment, novel dihydroindenoisoquinolines substituted with at least one electron withdrawing group are described. In another embodiment, novel dihydroindenoisoquinolines that are substituted with at least one nitrogen containing group are described.

Illustrative dihydroindenoisoquinolines described herein include compounds of the formula

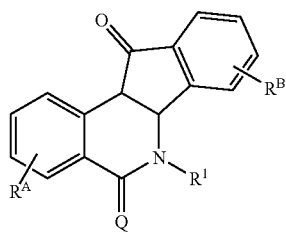

wherein Q, $R^A$, $R^B$, and $R^1$ are as described herein.

DETAILED DESCRIPTION

Described herein are processes for preparing indenoisoquinolines and dihydroindenoisoquinolines. The processes described herein are suitable for preparing a wide variety of substituted indenoisoquinolines and dihydroindenoisoquinolines. Also described herein are novel dihydroindenoisoquinolines. In one embodiment, the indenoisoquinolines and dihydroindenoisoquinolines are substituted with at least one electron withdrawing substituent, including but not limited to halogen, hydroxy, $C_1$-$C_6$ alkanoyloxy, optionally substituted benzoyloxy, alkylcarbonylamino, N-($C_1$-$C_6$ alkyl)alkylcarbonylamino, cyano, nitro, $C_1$-$C_6$ alkylsulfonyl, and/or a group such as —$N_3$, —$CO_2R^{4'}$, —$CONR^{5'}R^{6'}$, —P(O)($OR^{4'}$)$_2$, —P(O)($NR^{4'}R^{5'}$)$_2$, and —P(O)($NR^{4'}R^{5'}$)($OR^{4'}$), where $R^{4'}$, $R^{5'}$, and $R^{6'}$ are each independently selected in each occurrence from hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl, and the like. In one aspect, the electron withdrawing substituent is nitro. In another embodiment, the indenoisoquinolines and dihydroindenoisoquinolines are substituted with at least one nitrogen containing substituent, such as amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, azido, and the like.

The present invention provides a process for preparing a dihydroindenoisoquinolone. In one embodiment, the process comprises the step of cyclizing a compound of the formula

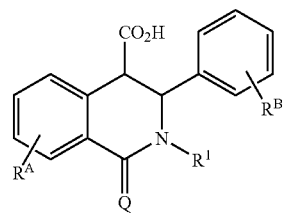

by reacting the compound with phosphorus pentoxide in an aprotic solvent. It is appreciated that Q may be oxygen or sulfur. Further, $R^1$ may be selected from the group consisting of hydrogen and a radical —$(CH_2)_mZ$, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of —$N_3$, —$CO_2R^4$, —$CONR^5R^6$, —P(O)($OR^4$)$_2$, —P(O)($NR^4R^5$)$_2$, and —P(O)($NR^4R^5$)($OR^4$), where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Further, $R^A$ may represent 1-4 substituents each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —P(O)($OR^{4'}$)$_2$, —P(O)($NR^{4'}R^{5'}$)$_2$, and —P(O)($NR^{4'}R^{5'}$)($OR^{4'}$), where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Alternatively, $R^A$ may represent 2-4 substituents where 2 of the substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$—P(O)($OR^{4'}$)$_2$, —P(O)($NR^{4'}R^{5'}$)$_2$, and —P(O)($NR^{4'}R^{5'}$)($OR^{4'}$), where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

It is further appreciated that $R^B$ may represent 1-4 substituents each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z" is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or Alternatively, $R^B$ may represent 2-4 substituents where 2 of the substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m''}Z''$, where m" is an integer from 0-6 and Z" is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl) alkylcarbonylaminoalkyl, cyano, nitro, $C_1$-$C_6$ alkylsulfonyl, optionally substituted phenyl, optionally substituted phenoxy, and optionally substituted heteroaryl; or Z" is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_g$ cycloalkyl, $C_1$-$C_6$ haloalkyl, optionally substituted phenyl, and optionally substituted phenyl-$C_1$-$C_6$ alkyl is described.

The starting compound used in the cyclizing step may have at least one of $R^A$ being nitro, or at least one of $R^B$ being nitro.

In one aspect, the cyclizing step may include an aprotic solvent selected from the group consisting of chlorinated solvents, carbon disulfide, aromatic solvents, ether solvents, ester solvents, nitrile solvents, polar aprotic solvents, and combinations thereof. In another aspect, the cyclizing step may include a chlorinated aprotic solvent.

In another embodiment, the process may comprise the steps of (a) activating a compound of the formula

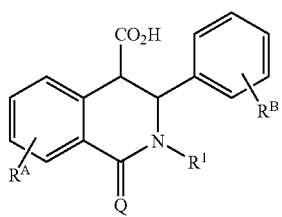

by reacting the compound with a carboxylic acid activating reagent to form an activated carboxylic acid derivative; and (b) cyclizing the activated carboxylic acid derivative by reacting the activated carboxylic acid derivative with a Lewis acid. The formula of the compound used in this embodiment may be any one of the alternatives described hereinabove.

In one aspect, the activating step may include the carboxylic acid activating reagent selected from the group consisting of acid halide forming reagents, N-hydroxysuccinimidyl ester forming reagents, Lewis acid activators, dehydrating agents, and combinations thereof. Alternatively, the activating step may include the carboxylic acid activating reagent is an acid halide forming reagent.

In another aspect, the cyclizing step may include the Lewis acid selected from the group consisting of aluminum halides, boron halides, iron halides, and combinations thereof.

In yet another embodiment, the present invention includes a compound of the formula

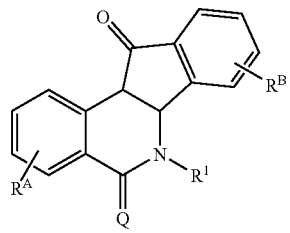

wherein

Q is oxygen or sulfur;

$R^1$ is selected from the group consisting of hydrogen and a radical —$(CH_2)_m Z$, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of —$N_3$, —$CO_2R^4$, —$CONR^5R^6$, —$P(O)(OR^4)_2$, —$P(O)(NR^4R^5)_2$, and —$P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Further, $R^A$ represents 1-4 substituents each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Alternatively, $R^A$ represents 2-4 substituents where 2 of the substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Further, $R^B$ represents 1-4 substituents each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

Alternatively, $R^B$ represents 2-4 substituents where 2 of the substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N-($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N-($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —$N_3$, —$CO_2R^{4''}$, —$CONR^{5''}R^{6''}$, —$P(O)(OR^{4''})_2$, —$P(O)(R^{4''}R^{5''})_2$, and —$P(O)NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl is described.

It is further provided that at least one of $R^A$ or $R^B$ is an electron withdrawing substituent or a nitrogen-containing substituent.

In one form, the compound having the nitrogen-containing substituent being nitro or optionally substituted amino.

Molecular modeling of the indenoisoquinolines in a ternary complex with DNA and top1 indicates few hydrogen-bonding contacts between the polycyclic backbone of the inhibitor and top1 (see Nagarajan M., et al., *J. Med. Chem.* 2003, 46, 5712). Without being bound by theory, it is appreciated that keeping strictly with the indenoisoquinoline pharmacophore, there may be little chance of increasing the potency of these compounds using hydrogen-bonding contacts alone. Examination of the recently published crystal structure comprising topotecan, DNA, and top1 suggests that approximately 60% of the solvent-accessible surface of topotecan is involved in n-stacking interaction with the DNA bases above and below insertion. (Staker B, et al., *Proc. Natl. Acad. Sci. U.S.A.* 2002, 99, 15387). It is also appreciated that the intercalation of topotecan, and by analogy the indenoisoquinolines, may be driven in large part by favorable n-stacking interactions between the DNA bases and the aromatic rings of the molecule. (Shetty A, et al., *J. Am. Chem. Soc.* 1996, 118, 1019). Effectively increasing the affinity for 7-stacking may increase the potency of the indenoisoquinolines described herein. The interaction of nitrated aromatic compounds with DNA has been reported. (Vance W, Levin D, *Environmental Mutagenesis* 1984, 6, 797). However, nitration of compounds to capitalize on or increase π-stacking interactions with top1 inhibitors has not been described.

The following examples further illustrate exemplified embodiments and aspects the invention. The examples illustrated herein are intended only to further describe the invention and should not be interpreted as limiting the invention.

EXAMPLE 1

Carboxylic acids 8, 9, 10, and 11 were prepared through condensation of the appropriate Schiff bases with 4-nitrohomophthalic anhydride (3) (see Whitmore W, Cooney R, *J. Am. Chem. Soc.* 1944, 66, 1237, incorporated herein by reference) (Scheme 1).

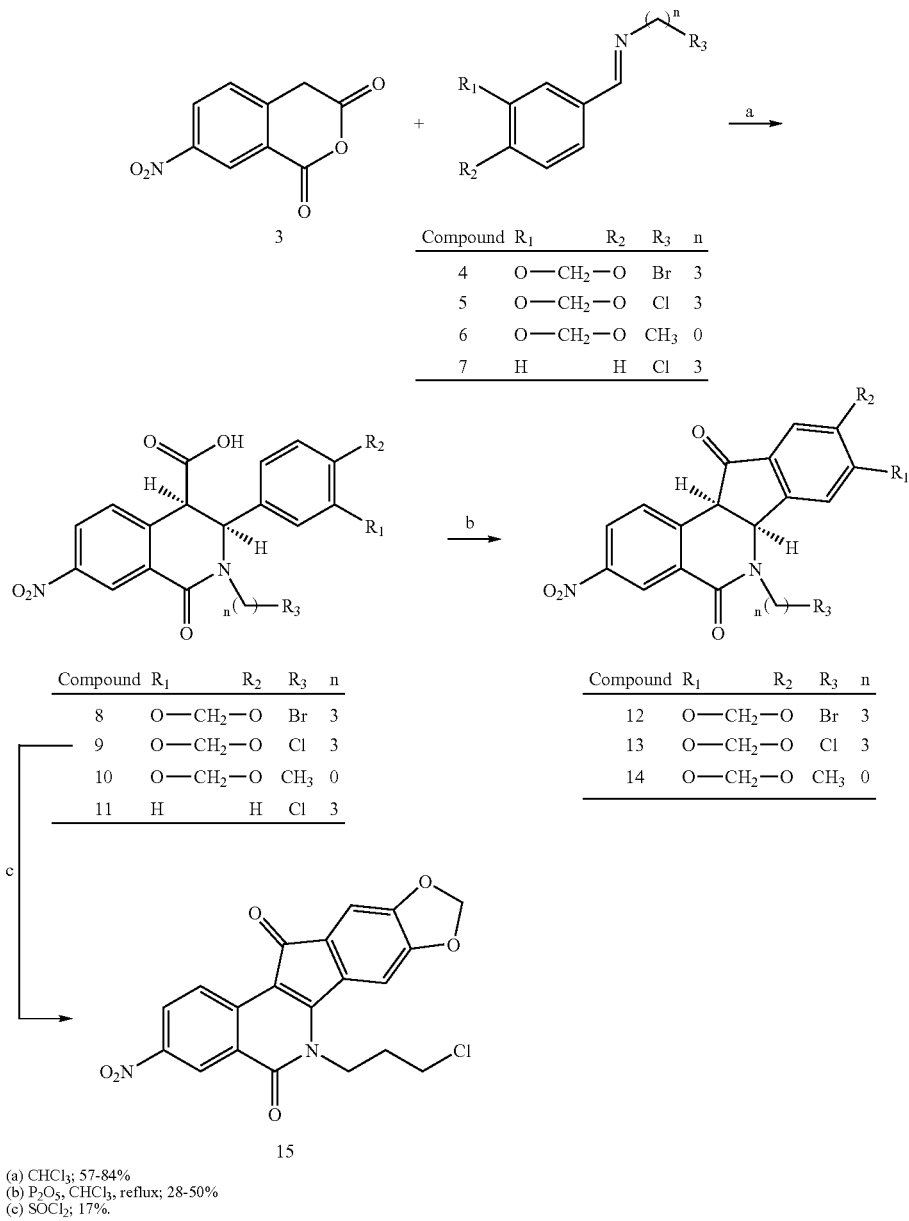

Scheme 1

(a) CHCl$_3$; 57-84%
(b) P$_2$O$_5$, CHCl$_3$, reflux; 28-50%
(c) SOCl$_2$; 17%.

Treatment of these carboxylic acids with thionyl chloride to induce Friedel-Crafts ring closure and dehydrogenation (Cushman M, Cheng L, *J. Org. Chem.* 1978, 43, 3781) was unsuccessful or resulted in a poor yield of the corresponding indenoisoquinolines. Similarly, using Eaton's reagent (see Strumberg D, et al., *J. Med. Chem.* 1999, 42, 446), or polyphosphoric acid (see Cushman M; Cheng L, *J. Org. Chem.* 1978, 43, 286), to affect "Friedel-Crafts" type ring closure without oxidation to provide dihydroindenoisoquinolines 12, 13, and 14 was unsuccessful. However, ring closure was accomplished using P$_2$O$_5$ as a dehydrating agent (see Cushman M, Cheng L, *J. Org. Chem.* 1978, 43, 3781, incorporated herein by reference) to provide the corresponding dihydroindenoisoquinolines without oxidation. This ring closure may be performed in a wide variety of non-protic solvents. The corresponding indenoisoquinolines may be prepared by oxidation using conventional oxidizing or dehydrogenating agents. Substitution of the ring nitrogen may be accomplished by appropriate substitution of starting material, or by the introduction or modification of substituents on either the indenoisoquinolines or dihydroindenoisoquinolines described herein.

EXAMPLE 2

Azide Substitution and Oxidation of Dihydroindenoisoquinoline

It was found that treatment of dihydroindenoisoquinoline 12 treated with NaN$_3$ in DMSO provided the corresponding alkyl azide substituent, and also oxidized 12 from the dihydroindenoisoquinoline skeleton to the indenoisoquinoline skeleton of 16 (Scheme 2).

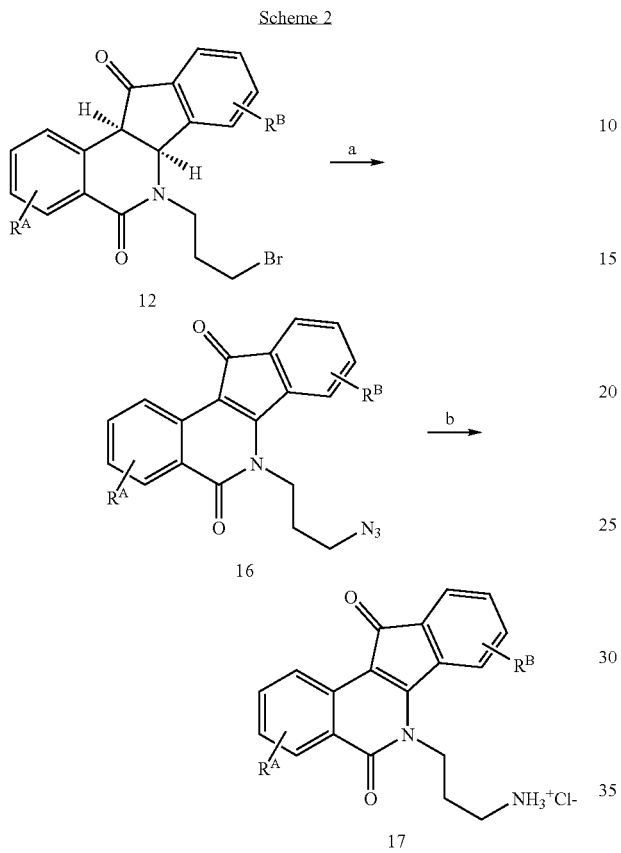

(a) NaN₃, DMSO, 80%;
(b) 1. P(OEt)₃, benzene, reflux;
2. 3 M HCl/MeOH, reflux, 74%.

Illustratively, $R^A$ is $NO_2$, such as 3-$NO_2$, and $R^B$ is one or more alkoxy or alkylenedioxy groups, such as 8,9-methylene dioxy. Subsequently, Staudinger reduction (Cushman M, et al., *J. Med. Chem.* 2000, 43, 3688-3698, incorporated herein by reference) of azide 16 proceeded to provide 17, which was isolated as its hydrochloride salt. Other conventional reducing agents may also be used, including but not limited to other phosphites, borohydrides, aluminum hydrides, hydrogenation, and the like. It is understood that appropriate protection of other functional groups using conventional procedure such as those described in Greene & Wuts, "Protective Groups in Organic Synthesis, Second Edition" John Wiley & Sons, Inc. (NY 1991), incorporated herein by reference, such as the carbonyl groups, may be necessary for some reducing reagents.

EXAMPLE 3

Replacement of Nitro Substituent with Electron-Donating Aniline-Type Amino Functionality Compound 18 was synthesized (Scheme 3) with the nitro substituent replaced with an electron-donating aniline-type amino functionality.

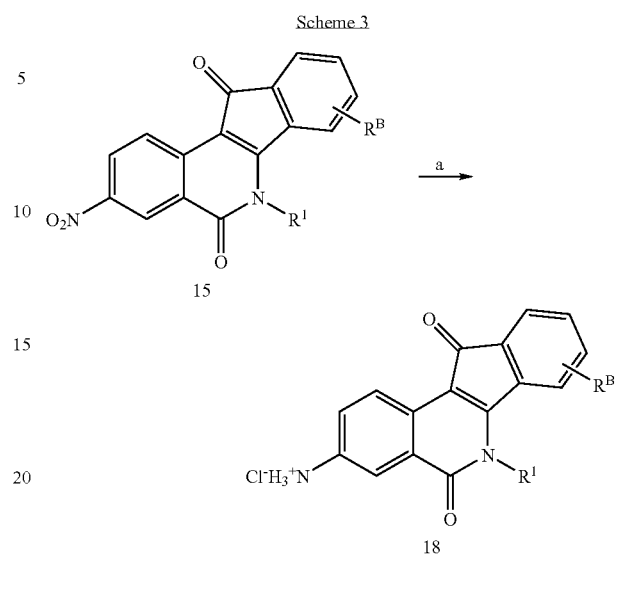

(a) 1. Raney Ni, HCO2H, acetone, DMF;
2. 2 M HCl/Et2O, 40%.

Illustratively, $R^B$ is one or more alkoxy or alkylene dioxy groups, such as 8,9-methylenedioxy and R' is hydroalkyl, such as chloropropyl.

EXAMPLE 4

Direct Nitration of Indenoisoquinolines

Initially unsubstituted indenoisoquinolines may also be directly nitrated, as described in Scheme 4.

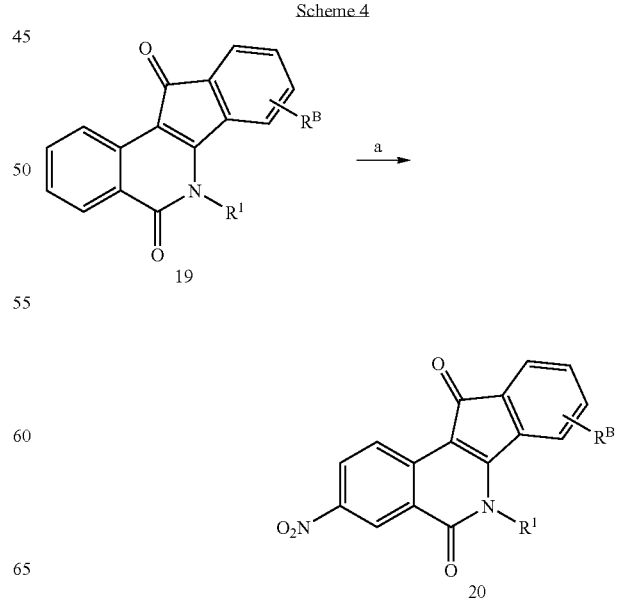

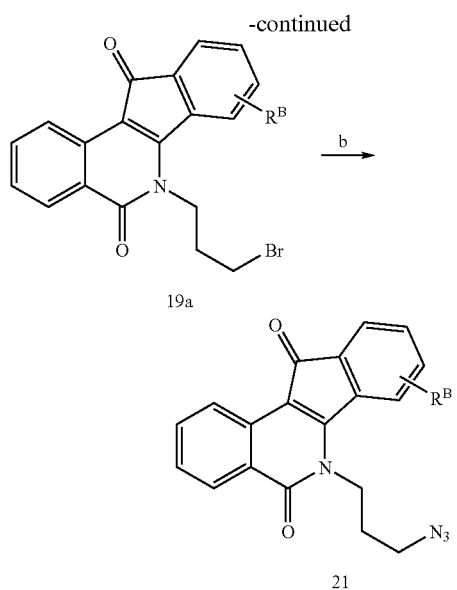

(a) 1. Raney-Ni, HCO2H, acetone, DMF;
2. 2 M HCl/Et2O, 40%.

$R^B$ is as defined herein, and illustratively H, R' is illustratively halo alkyl, such as bromo propyl. Attempted conversion of compound 21 to the desired nitro compound provided only an inseparable mixture of compounds and isomers.

EXAMPLE 5

Oxidation Friedel-Crafts Acylation Cyclization

Compound 22 was synthesized from compound 11 (Scheme 5) after initial treatment with thionyl chloride, followed by aluminum chloride in an oxidation Friedel-Crafts acylation cyclization.

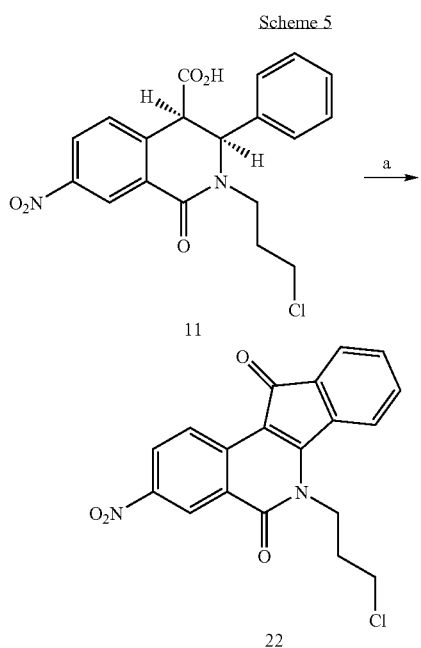

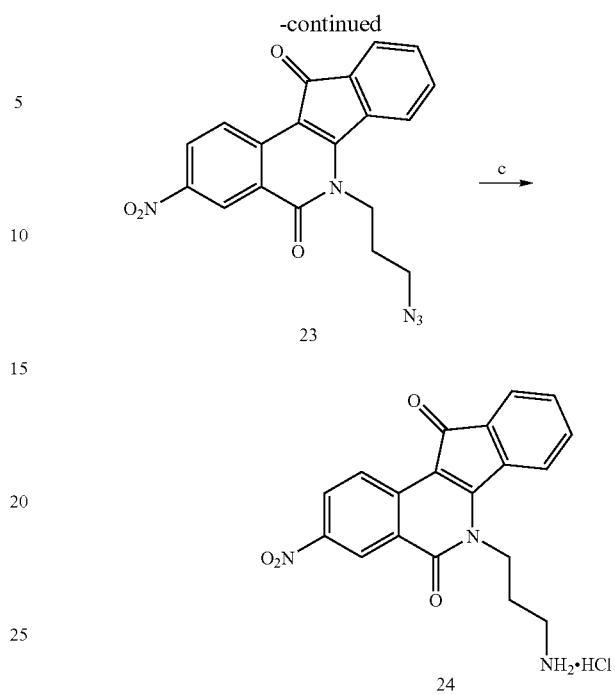

(a) (1) SOCl₂, benzene
(2) AlCl₃; 57%
(b) NaN₃, DMSO. 100° C.; 98%
(c) (1) P(OEt)₃, benzene, reflux
(2) 3 N HCl/MeOH, reflux; 86%.

It is appreciated that the exact sequence of steps involving (1) acid chloride formation, (2) dehydrogenation, and (3) intramolecular Friedel-Crafts acylation may be varied.

EXAMPLE 6

Alternative Synthesis of Nitrated Indenoisoquinolines

In another aspect of the present invention, a novel process for synthesis of nitrated indenoisoquinolines is described. This novel process is based on the reaction to incorporate electron-withdrawing groups on the isoquinoline and indenone rings (Scheme 6).

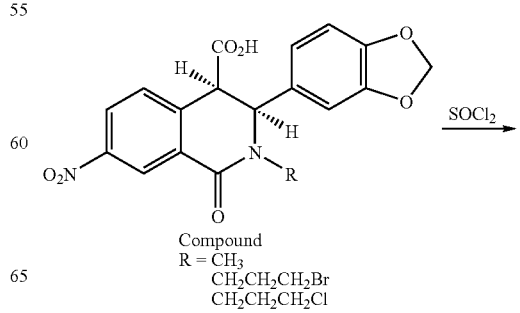

Compound
R = CH₃
CH₂CH₂CH₂Br
CH₂CH₂CH₂Cl

-continued

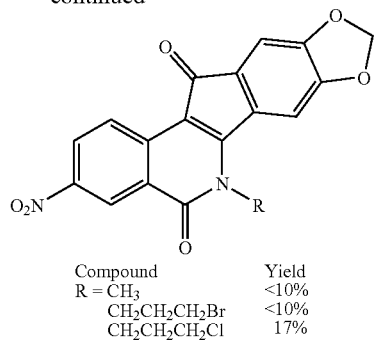

| Compound | Yield |
|---|---|
| R = CH₃ | <10% |
| CH₂CH₂CH₂Br | <10% |
| CH₂CH₂CH₂Cl | 17% |

Preparations of compounds with three different lactam substituents were attempted (Scheme 6). For the methyl- and 3-bromopropyl-substituted isoquinolinic acids, treatment with thionyl chloride under conditions previously reported by Cushman and Cheng (J. Org. Chem. 1978. 43, 3781-3783) led to a complex reaction mixture with the yield of the corresponding indenoisoquinoline being less than 10% (estimated by thin layer chromatography: $SiO_2/CHCl_3$). The 3-chloropropyl-substituted isoquinolinic acid provided the corresponding indenoisoquinoline in 17% yield (isolated) with the increased yield relative to the other compounds attributed to the chlorine substituent's diminished reactivity towards competing reactions (i.e. electrophilic aromatic substitution and nucleophilic displacement). It was also observed that the nitrated isoquinolinic acids are less stable than the electron-rich isoquinolinic acids. The nitrated isoquinolinic acids were observed to readily decarboxylate in DMSO at room temperature, and further it was observed that the methyl and 3-bromopropyl substituted compounds decarboxylated faster than the 3-chloropropyl substituted compound. However, it is appreciated that $SOBr_2$ may give superior yields of indenoisoquinoline than was observed with $SOCl_2$.

EXAMPLE 7

$P_2O_5$ Dehydration Results

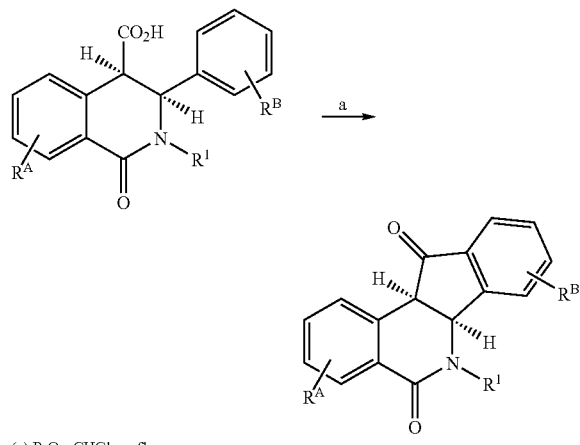

(a) $P_2O_5$, $CHCl_3$, reflux.

Illustrative compounds include the following.

| $R^A$ | $R^B$ | $R^1$ | Yield |
|---|---|---|---|
| 3-NO₂ | 8,9-(OCH₂O) | CH₃ | 48 |
| 3-NO₂ | 8,9-(OCH₂O) | (CH₂)₃Br | 50 |
| 3-NO₂ | 8,9-(OCH₂O) | (CH₂)₃Cl | 25 |

The results in Scheme 7 indicate that the $P_2O_5$ protocol for inducing ring closure was superior to the thionyl chloride method for all three investigated compounds and provided yields 2 to 5 times greater than what could be obtained or estimated from the thionyl chloride method. $R^B$ is illustratively one or more alkoxy and/or alkylendioxy groups, such as 8,9-methylendioxy. The dihydroindenoisoquinolines may be readily converted into their oxidized counterparts under a variety of conventional conditions. Various conditions to accomplish this transformation include the quinone class of oxidants, selenium dioxide, covalent attachment of any sulfur compound followed by oxidative elimination, introduction of any leaving group at the benzylic position and elimination, heating (either neat or in solution, such as DMSO), dissolving in DMSO and stirring at room temperature, treating with sodium azide in DMSO, and the like.

The cyclization may be accomplished with any activated carbonyl group including carboxylic acid halides, esters of N-hydroxysuccinimide, and a variety of Lewis acid activators, and dehydrating agents. Alternatively, the benzylic positions of the isoquinolinic acid may be first oxidized and cyclization induced (see, Cushman, M.; Cheng, L. J. Org. Chem. 1978, 43, 3781-3783, incorporated herein by reference). A variety of solvents may be utilized for the $P_2O_5$ protocol including, but not limited to, methylene chloride, carbon tetrachloride, carbon disulfide, benzene, substituted benzenes, acetonitrile, ether, dioxane, tetrahydrofuran, ethyl acetate, dimethylformamide, and DMSO. In one aspect, the solvent is an aprotic solvent. In another aspect, the solvent is apolar aprotic solvent, such as DMSO, DMF, NMP, and the like. In another aspect, the solvent is a chlorinated solvent. It is appreciated that combinations of the foregoing solvents may also be used in the processes described herein.

EXAMPLE 8

Alternative Ring Closure Method

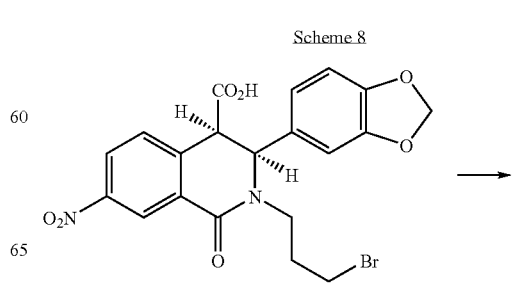

-continued

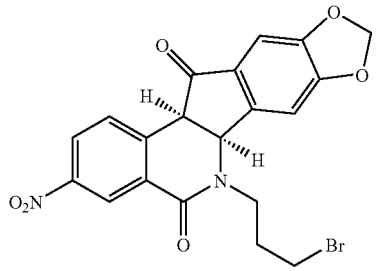

| Conditions | Yield (TLC analysis) |
|---|---|
| Eatons's reagent | complex |
| polyphosphoric acid at ambient temperature | complex |
| polyphosphoric acid at 100° C. | complex |

The results indicated (Scheme 8) that for Eaton's reagent and polyphosphoric acid, previously reported conditions (Cushman, M.; Cheng, L. *J. Org. Chem.* 1978, 43, 3781-3783; J. Org. Chem. 1978, 43, 286-288) for effecting ring closure to provide dihydroindenoisoquinolines resulted in a complex reaction mixture for the 3-bromopropyl-substituted isoquinolinic acid. However, heating the cis-acid in chloroform over $P_2O_5$ resulted in a 50% yield of the ring-closed product (see EXAMPLE 7). The method of EXAMPLE 7 was further superior to the thionyl chloride protocol (see EXAMPLE 6) based on yield and simplicity of purification (requiring only filter, wash, concentrate, and precipitate steps). The methyl- and 3-chloropropyl-substituted compounds were also subjected to the $P_2O_5$ protocol and the results are provided in Scheme 9.

EXAMPLE 9

Cyclization of Brominated Isoquinolinic Acid

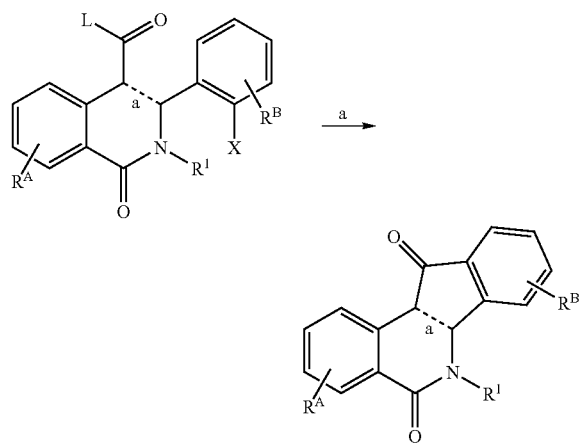

(a) base.

In another embodiment, ring closure to the indenoisoquinoline or dihydroindenoisoquinoline is accomplished by treatment with a strong base, such as an organometallic base, including a BuLi. In Scheme 9, treatment of an appropriately substituted isoquinolinic acid (either oxidized at the benzylic position where bond a is a double bond, or the cis-dihydro counterpart where bond a is a single bond) may undergo metal exchange with a group X, such as an halogen group, and provide a nucleophile in sufficient proximity of the carboxylic acid with a suitable leaving group (L) attached. This leaving group may be in the form of an ester, amide, acid halide, or similar carboxylic acid derivative. Displacement of the leaving group by the nucleophile may then provide either the corresponding indenoisoquinoline or the dihydroindenoisoquinoline. It is appreciated that ortho-directed lithiation may also be used to promote cyclization by displacing the leaving group.

EXAMPLE 10

Oxidative Acylation-Ring Closure

In another embodiment of the present invention, a procedure that includes electron neutral and deficient aromatic rings is described (see Scheme 10).

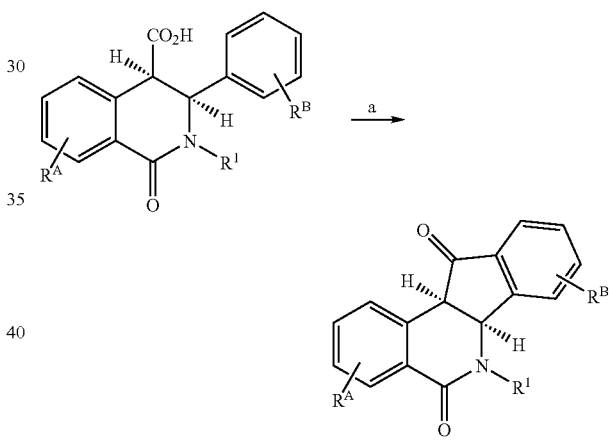

(a) 1. $SOCl_2$, benzene, reflux;
2. $AlCl_3$, nitrobenzene, 100° C.

Illustrative compounds include the following.

| $R^A$ | $R^B$ | $R^1$ | Yield |
|---|---|---|---|
| 3-$NO_2$ | H | $(CH_2)_3Cl$ | 57 |
| 2,3-$(OCH_3)_2$ | H | $(CH_2)_3Cl$ | 95 |
| 2,3-$(OCH_2O)$ | H | $(CH_2)_3Cl$ | 49 |
| H | 9-Br | $(CH_2)_3Cl$ | 25 |

Treatment of various cis-isoquinolinic acids with thionyl chloride in benzene generated the corresponding acid chloride, which underwent an oxidative cyclization in the presence of aluminum chloride to provide the corresponding indenoisoquinolines in high yield. It is appreciated that this method may be the only route to compounds having particularly substituted isoquinoline rings and/or unsubstituted indenone rings. In addition, this method has been shown to proceed with compounds possessing electron-withdrawing substituents on either of the phenyl rings.

It is appreciated that the 9-bromo substituent may provide a suitable synthon for the introduction of other substituents though halogen-metal exchange, nucleophilic attack, and/or through other types of palladium, copper, Stille, and like coupling reactions to provide other substituted variants ($R^B$) of the compounds described herein.

In addition, the activation step may be performed in a variety of solvents including but not limited to benzene, substituted benzenes, chlorinated solvents, chloroform, ether, THF, dioxane, methylene chloride, carbon disulfide, and the like, and mixtures thereof. Futhermore, ring closure and oxidation may be performed with any conventional or unconventional Lewis acid, including but not limited to $BF_3$, $AlCl_3$, $SnCl_4$, $TiCl_4$, and the like, with various metals, such as iron, tungsten, zinc, and the like, and/or with other forms of oxidizing agents described herein. The reactions may be performed at a variety of conventional temperautres including those in the range from about 0 to about 220° C.

EXAMPLE 12

Biological Evaluation In Vitro

The indenoisoquinolines described herein were examined for antiproliferative activity against the human cancer cell lines in the National Cancer Institute screen, in which the activity of each compound was evaluated with approximately 55 different cancer cell lines of diverse tumor origins. The GI50 values obtained with selected cell lines, along with the mean graph midpoint (MGM) values, are summarized in Table 1. The MGM is based on a calculation of the average GI50 for all of the cell lines tested (approximately 55) in which GI50 values below and above the test range ($10^{-8}$ to $10^{-4}$ molar) are taken as the minimum ($10^{-8}$ molar) and maximum ($10^{-4}$ molar) drug concentrations used in the screening test. The relative potencies of the compounds described herein in the production of topoisomerase I-mediated DNA cleavage are also listed in Table 1.

The data in Table 1 demonstrate that the incorporation of a nitro substituent in the isoquinoline ring provides cytotoxic compounds and top1 inhibition. The activities of dihydroindenoisoquinolines 12 and 13 (16 and 18 nm, respectively), in particular, are each an order of magnitude greater than their di(methoxy) substituted counterpart (see Jayaraman M, et al., *J. Med. Chem.* 2002, 45, 242; Cushman M, et al., *J. Med. Chem.* 2000, 43, 3688-3698; Nagarajan M, et al., *J. Med. Chem.* 2004, 47, 5651-5661). The corresponding dihydroindenoisoquinolines were less active than their indenoisoquinoline counterparts in the top1 inhibition assay. It is appreciated that this lower activity may be due to the accepted requirement of planarity for potent top1 inhibition. This balance between cytotoxicity in the cellular assay and inhibition of top1 in the cell-free assay (compare for example compounds 13 and 15) has been observed earlier (see Strumberg D, et al., *J. Med. Chem.* 1999, 42, 446; Jayaraman M, et al., *J. Med. Chem.* 2002, 45, 242). Without being bound by theory, it is understood that a possible explanation for the difference may be that the dihydroindenoisoquinolines, especially those with nitro substituents, might be serving as prodrugs in the cell-based cytotoxicity assay where differences in uptake and distribution may cause the enhanced cytotoxicity. After distribution within the cell, these dihydro prodrugs may be oxidized to the indenoisoquinolines, which subsequently inhibit top1.

With regard to indenoisoquinolines such as 15, 16, and 17 that posses a nitro substituent on the isoquinoline ring and a methylenedioxy-substituted indenone ring, these molecules display potent cytotoxicities (0.832 μM, 98 nM, and 90 nM respectively) and top1 inhibition (+++, ++++, and ++++ respectively). These compounds outperformed the dihydroindenoisoquinolines in the top1 inhibition assay and were superior in all respects to certain electron rich analogues that lack nitro substituents (see Kohlhagen G, et al., Mol. Pharmacol. 1998, 54, 50; Jayaraman M, et al., *J. Med. Chem.* 2002, 45, 242; Cushman M, et al., *J. Med. Chem.* 2000, 43, 3688-3698; Nagarajan M, et al., *J. Med. Chem.* 2004, 47, 5651-5661). Compound 18 (25 μM MGM) was also prepared with the nitro functionality replaced with an aniline-type nitrogen. As indicated in Table 1, activity across all cell lines was poorer upon switching from an electron-withdrawing to an electron-donating substituent.

Removal of the methylenedioxy substituent from the indenone ring appeared to lower activity in this series. A direct comparison of compounds 16 (98 nM) and 23 (13.5 μM) indicates that a synergistic effect might be occurring between the nitro and methylenedioxy substituents. It is appreciated that the activity of nitrated compounds 20, 22, and 23 (40, 18.2, and 13.5 μM respectively) may be improved by including an alkylamine group on the nitrogen, as shown by alkylamine 24 (0.245 μM). This data further supports the past structure-activity relationships (SAR) determination and reinforces the role of the methylenedioxy ring, when the isoquinolone moiety is nitrated.

Although the invention has been described in detail with reference to certain illustrated embodiments, variations and modifications exist within the scope and spirit of the present invention as described and defined in the following claims.

TABLE 1

Cytotoxicities and Topoisomerase I Inhibitory Activities of Indenoisoquinoline Analogs.[14]

| | cytotoxicity (GI50 in μM)[a] | | | | | | | | | |
|---|---|---|---|---|---|---|---|---|---|---|
| compd | lung HOP-62 | colon HCT-116 | CNS SF-268 | melanoma UACC-62 | ovarian OVCAR-3 | renal SN12C | prostate DU-145 | breast MDA-MB-435 | MGM[b] | Top 1 Cleavage[c] |
| 12 | <0.010 | <0.010 | <0.010 | <0.010 | <0.010 | <0.010 | <0.010 | <0.010 | 0.016 ± 0.003 | + |
| 13 | <0.010 | <0.010 | <0.010 | <0.010 | <0.010 | <0.010 | <0.010 | <0.010 | 0.018 ± 0.001 | + |
| 14 | 0.158 | 0.014 | 0.024 | 0.026 | 0.03 | 0.033 | 0.05 | 0.107 | 0.105 ± 0.007 | +++ |
| 15 | 0.41 | 2.4 | 0.148 | 0.229 | 9.12 | 0.132 | 0.098 | 1.82 | 0.832 | +++ |
| 16 | <0.010 | <0.010 | <0.010 | <0.010 | <0.010 | <0.010 | <0.010 | <0.010 | 0.098 ± 0.06 | ++++ |
| 17 | <0.010 | <0.010 | <0.010 | 0.017 | 0.302 | <0.010 | <0.010 | 0.025 | 0.090 ± 0.04 | ++++ |
| 18 | NT | NT | >100 | >100 | >100 | >100 | NT | >100 | 25 | 0 |
| 20 | NT | 3.45 | >100 | >100 | >100 | >100 | >100 | >100 | 40 | 0 |
| 22 | 43.7 | 3.63 | 23.4 | 20.4 | 4.9 | 26.9 | 40.7 | 31.6 | 18.2 | NT |
| 23 | >100 | 8.13 | 79.4 | 44.7 | NT | 72.4 | >100 | >100 | 13.5 | NT |

TABLE 1-continued

Cytotoxicities and Topoisomerase I Inhibitory Activities of Indenoisoquinoline Analogs.[14]

| | cytotoxicity (GI50 in μM)[a] | | | | | | | | | |
|---|---|---|---|---|---|---|---|---|---|---|
| compd | lung HOP-62 | colon HCT-116 | CNS SF-268 | melanoma UACC-62 | ovarian OVCAR-3 | renal SN12C | prostate DU-145 | breast MDA-MB-435 | MGM[b] | Top 1 Cleavage[c] |
| 24 | 0.275 | 0.085 | 0.302 | 0.372 | 0.112 | 0.102 | 0.148 | 0.832 | 0.245 | NT |
| 25 | 1.3 | 35 | NT | 4.2 | 73 | 68 | 37 | 96 | 20 | ++ |

[a]The cytotoxicity GI50 values are the concentrations corresponding to 50% growth inhibition.
[b]Mean graph midpoint for growth inhibition of all human cancer cell lines successfully tested.
[c]The compounds were tested at concentrations ranging up to 10 μM. The activity of the compounds to produce top1-mediated DNA cleavage was expressed semi-quantitatively as follows: +: weak activity; ++: similar activity as the parent compound 25; +++ and ++++: greater activity than the parent compound 25; ++++: similar activity as 1 μM camptothecin.

What is claimed is:

1. A process for preparing a dihydroindenoisoquinolone of the formula

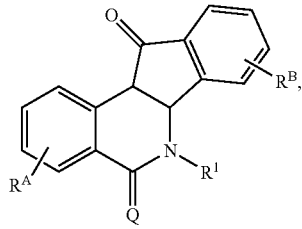

the process comprising the step of cyclizing a compound of the formula

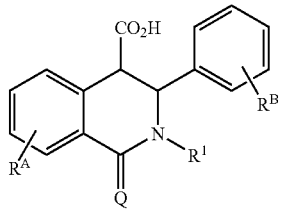

by reacting said compound with phosphorus pentoxide in an aprotic solvent;
wherein in said formulae Q is oxygen or sulfur;

$R^1$ is selected from the group consisting of hydrogen and a radical $-(CH_2)_m Z$, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $-N_3$, $-CO_2R^4$, $-CONR^5R^6$, $-P(O)(OR^4)_2$, $-P(O)(NR^4R^5)_2$, and $-P(O)(NR^4R^5)$ ($OR^4$), where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^A$ represents 1-4 substituents each independently selected from the group consisting of hydrogen and a radical $-(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of $-N_3$, $-CO_2R^{4'}$, $-CONR^{5'}R^{6'}$, $-P(O)(OR^{4'})_2$, $-P(O)(NR^{4'}R^{5'})_2$, and $-P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^A$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical $-(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of $-N_3$, $-CO_2R^{4'}$, $-CONR^{5'}R^{6'}$, $-P(O)$ (OR⁴')₂, —P(O)(NR⁴'R⁵')₂, and —P(O)(NR⁴'R⁵')(OR⁴'), where R⁴', R⁵', and R⁶' are each independently selected in each occurrence from the group consisting of hydrogen, C₁-C₆ alkyl, C₃-C₈ cycloalkyl, C₁-C₆ haloalkyl, optionally substituted phenyl, and optionally substituted phenyl-C₁-C₆ alkyl; and R^B represents 1-4 substituents each independently selected from the group consisting of hydrogen and a radical —(CH₂)_m''Z'', where m'' is an integer from 0-6 and Z'' is selected from the group consisting of halogen, hydroxy, C₁-C₆ alkanoyloxy, optionally substituted benzoyloxy, C₁-C₆ alkyl, C₁-C₆ alkoxy, C₃-C₈ cycloalkyl, C₃-C₈ cycloalkoxy, C₂-C₆ alkenyl, C₂-C₆ alkynyl, C₁-C₆ haloalkyl, C₁-C₆ haloalkoxy, C₃-C₈ halocycloalkyl, C₃-C₈ halocycloalkoxy, amino, C₁-C₆ alkylamino, (C₁-C₆ alkyl)(C₁-C₆ alkyl)amino, alkylcarbonylamino, N—(C₁-C₆ alkyl)alkylcarbonylamino, aminoalkyl, C₁-C₆ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, optionally substituted phenoxy, and optionally substituted heteroaryl; or Z'' is selected from the group consisting of —N₃, —CO₂R⁴'', —CONR⁵''R⁶'', —P(O)(OR⁴'')₂, —P(O)(NR⁴''R⁵'')₂, and —P(O)(NR⁴''R⁵'')(OR⁴''), where R⁴'', R⁵'', and R⁶'' are each independently selected in each occurrence from the group consisting of hydrogen, C₁-C₆ alkyl, C₃-C₈ cycloalkyl, C₁-C₆ haloalkyl, optionally substituted phenyl, and optionally substituted phenyl-C₁-C₆ alkyl; or R^B represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —(CH₂)_m''Z'', where m'' is an integer from 0-6 and Z'' is selected from the group consisting of halogen, hydroxy, C₁-C₆ alkanoyloxy, optionally substituted benzoyloxy, C₁-C₆ alkyl, C₁-C₆ alkoxy, C₃-C₈ cycloalkyl, C₃-C₈ cycloalkoxy, C₂-C₆ alkenyl, C₂-C₆ alkynyl, C₁-C₆ haloalkyl, C₁-C₆ haloalkoxy, C₃-C₈ halocycloalkyl, C₃-C₈ halocycloalkoxy, amino, C₁-C₆ alkylamino, (C₁-C₆ alkyl)(C₁-C₆ alkyl)amino, alkylcarbonylamino, N—(C₁-C₆ alkyl)alkylcarbonylamino, aminoalkyl, C₁-C₆ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, optionally substituted phenoxy, and optionally substituted heteroaryl; or Z'' is selected from the group consisting of —N₃, —CO₂R⁴'', —CONR⁵''R⁶'', —P(O)(OR⁴'')₂, —P(O)(NR⁴''R⁵'')₂, and —P(O)(NR⁴''R⁵'')(OR⁴''), where R⁴'', R⁵'', and R⁶'' are each independently selected in each occurrence from the group consisting of hydrogen, C₁-C₆ alkyl, C₃-C₈ cycloalkyl, C₁-C₆ haloalkyl, optionally substituted phenyl, and optionally substituted phenyl-C₁-C₆ alkyl is described.

2. The process of claim 1 wherein the cyclizing step includes the compound where at least one of R^A is nitro.

3. The process of claim 1 wherein the cyclizing step includes the compound where at least one of R^B is nitro.

4. The process of claim 1 wherein the cyclizing step includes an aprotic solvent selected from the group consisting of chlorinated solvents, carbon disulfide, aromatic solvents, ether solvents, ester solvents, nitrile solvents, polar aprotic solvents, and combinations thereof.

5. The process of claim 1 wherein the cyclizing step includes a chlorinated aprotic solvent.

6. A compound of the formula

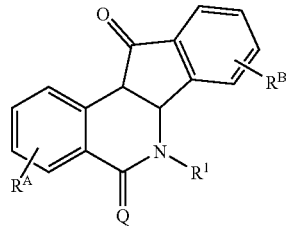

wherein

Q is oxygen or sulfur;

R¹ is selected from the group consisting of hydrogen and a radical —(CH₂)_m Z, where m is an integer from 0-6 and Z is selected from the group consisting of alogen, hydroxy, formyl, C₁-C₆ alkanoyloxy, optionally substituted benzoyloxy, C₁-C₆ alkyl, C₁-C₆ alkoxy, C₃-C₈ cycloalkyl, C₃-C₈ cycloalkoxy, C₂-C₆ alkenyl, C₂-C₆ alkynyl, C₁-C₆ haloalkyl, C₁-C₆ haloalkoxy, C₃-C₈ halocycloalkyl, C₃-C₈ halocycloalkoxy, amino, C₁-C₆ alkylamino, (C₁-C₆ alkyl)(C₁-C₆ alkyl)amino, alkylcarbonylamino, N—(C₁-C₆ alkyl)alkylcarbonylamino, aminoalkyl, C₁-C₆ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, optionally substituted phenoxy, and optionally substituted heteroaryl; or Z is selected from the group consisting of —N₃, —CO₂R⁴, —CONR⁵R⁶, —P(O)(OR⁴)₂, —P(O)(NR⁴R⁵)₂, and —P(O)(NR⁴R⁵)(OR⁴), where R⁴, R⁵, and R⁶ are each independently selected in each occurrence from the group consisting of hydrogen, C₁-C₆ alkyl, C₃-C₈ cycloalkyl, C₁-C₆ haloalkyl, optionally substituted phenyl, and optionally substituted phenyl-C₁-C₆ alkyl; or R^A represents 1-4 substituents each independently selected from the group consisting of hydrogen and a radical —(CH₂)_m'Z', where m' is an integer from 0-6 and Z' is selected from the group consisting of halogen, hydroxy, C₁-C₆ alkanoyloxy, optionally substituted benzoyloxy, C₁-C₆ alkyl, C₁-C₆ alkoxy, C₃-C₈ cycloalkyl, C₃-C₈ cycloalkoxy, C₂-C₆ alkenyl, C₂-C₆ alkynyl, C₁-C₆ haloalkyl, C₁-C₆ haloalkoxy, C₃-C₈ halocycloalkyl, C₃-C₈ halocycloalkoxy, amino, C₁-C₆ alkylamino, (C₁-C₆ alkyl)(C₁-C₆ alkyl)amino, alkylcarbonylamino, N—(C₁-C₆ alkyl)alkylcarbonylamino, aminoalkyl, C₁-C₆ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, optionally substituted phenoxy, and optionally substituted heteroaryl; or Z' is selected from the group consisting of —N₃, —CO₂R⁴', —CONR⁵'R⁶', —P(O)(OR⁴')₂, —P(O)(NR⁴'R⁵')₂, and —P(O)(NR⁴'R⁵')(OR⁴'), where R⁴', R⁵', and R⁶' are each independently selected in each occurrence from the group consisting of hydrogen, C₁-C₆ alkyl, C₃-C₈ cycloalkyl, C₁-C₆ haloalkyl, optionally substituted phenyl, and optionally substituted phenyl-C₁-C₆ alkyl; or R^A represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; and $R^B$ represents 1-4 substituents each independently selected from the group consisting of hydrogen and a radical —$(CH_2)_{m''}Z''$, where m" is an integer from 0-6 and Z" is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z" is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^B$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m''}Z''$, where m" is an integer from 0-6 and Z" is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z" is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl;

providing that at least one of $R^A$ or $R^B$ is a nitrogen-containing substituent or an electron withdrawing substituent.

7. The compound of claim 6 wherein at least one of $R^A$ or $R^B$ is a nitrogen-containing substituent selected from the group consisting of nitro and optionally substituted amino.

8. The compound of claim 6 wherein at least one of $R^A$ is nitro.

9. The compound of claim 6 wherein at least one of $R^B$ is nitro.

10. The process of claim 1 wherein at least one of $R^A$ or $R^B$ is a nitrogen-containing substituent or an electron-withdrawing substituent.

* * * * *

UNITED STATES PATENT AND TRADEMARK OFFICE
CERTIFICATE OF CORRECTION

PATENT NO. : 7,495,100 B2
APPLICATION NO. : 11/125723
DATED : February 24, 2009
INVENTOR(S) : Mark S. Cushman, Andrew F. Morrell and Yves G. Pommier It is certified that error appears in the above-identified patent and that said Letters Patent is hereby corrected as shown below:

Col. 24, line 20 change "alogen," to --halogen,--

Signed and Sealed this

Twelfth Day of May, 2009

JOHN DOLL
*Acting Director of the United States Patent and Trademark Office*